US00PP29834P3

(12) United States Plant Patent
Bourne

(10) Patent No.: US PP29,834 P3
(45) Date of Patent: Nov. 13, 2018

(54) ***DIANTHUS* PLANT NAMED 'WP15 PIE41'**

(50) Latin Name: ***Dianthus* x *allwoodii* hort.**
Varietal Denomination: WP15 PIE41

(71) Applicant: Plant Genetics International Ltd., Hambrook, West Sussex (GB)

(72) Inventor: Carolyn Grace Bourne, Devon (GB)

(73) Assignee: Plant Genetics International Ltd., Hambrook (GB)

( * ) Notice: Subject to any disclaimer, the term of this patent is extended or adjusted under 35 U.S.C. 154(b) by 0 days.

(21) Appl. No.: 15/731,062

(22) Filed: Apr. 12, 2017

(65) Prior Publication Data

US 2017/0303456 P1 Oct. 19, 2017

(30) Foreign Application Priority Data

Apr. 15, 2016 (QZ) ..... PBR 2016/0940

(51) Int. Cl.
*A01H 5/02* (2018.01)
*A01H 6/30* (2018.01)

(52) U.S. Cl.
USPC ..... Plt./273
CPC ..... *A01H 5/02* (2013.01); *A01H 6/305* (2018.05)

(58) Field of Classification Search
USPC ..... Plt./273, 272, 274, 279
CPC ..... A01H 5/0233; A01H 5/02; A01H 5/0227; A01H 5/00; A01H 6/305
See application file for complete search history.

(56) References Cited

PUBLICATIONS

Missouri Botanical Garden *Dianthus* (*Allwoodii* Alpinus Group), retrieved on Apr. 9, 2018, retrieved from the Internet at http://www.missouribotanicalgarden.org/PlantFinder/PlantFinderDetails.aspx?taxonid=259721&isprofile=0&, 2 pp. (Year: 2018).*

* cited by examiner

*Primary Examiner* — June Hwu
(74) *Attorney, Agent, or Firm* — Bethany R. Roahrig; Barbara Campbell; Cochran Freund & Young LLC

(57) ABSTRACT

A new cultivar of *Dianthus* plant named 'WP15 PIE41' that is characterized by a compact mounding habit, large single white flowers with a lime-colored eye, blooming from May through October, with a medium, sweet fragrance, glaucous blue green foliage, suitable for use as a flowering plant in pots and containers as well as for use as a cut flower and in bouquets, is disclosed.

2 Drawing Sheets

Genus and species: *Dianthus* x *allwoodii* hort.
Variety denomination: 'WP15 PIE41'.

CROSS REFERENCE TO RELATED APPLICATIONS

This application claims the benefit of priority under 35 U.S.C. 119 (f) to the application for European Community Plant Variety Rights which was filed for the instant plant variety on Apr. 15, 2016, File Number 2016/0940.

BACKGROUND OF THE NEW PLANT

The present invention relates to a new and distinct cultivar of hardy *Dianthus,* commonly known as Garden Pink, but selected for its unique large single flowers. The new cultivar can be grown for use as a flowering plant for pots and containers and for planting in the garden and landscape. The new cultivar is known botanically as *Dianthus* x *allwoodii* hort. and will be referred to hereinafter by the cultivar name 'WP15 PIE41'.

'WP15 PIE41' is a complex hybrid plant that is the product of a long term breeding program conducted in a cultivated area of Houndspool, Dawlish, Devon, United Kingdom. 'WP15 PIE41' was selected in 2008 for its single large flowers with a lime-colored eye, medium, sweet fragrance and glaucous blue-green foliage.

'WP15 PIE41' arose and was selected as a seedling which resulted from the open pollination of a prior selected *Dianthus.* The female parent is *Dianthus* code name 'PIE.017' (unpatented and unreleased). The female parent is grown within the inventor's stock of breeding lines.

Asexual reproduction of 'WP15 PIE41' was first accomplished in 2008 in a cultivated area of Houndspool, United Kingdom using the propagation method of shoot cuttings. 'WP15 PIE41' has been determined to be stable and reproduces true to type in successive generations of asexual propagation.

SUMMARY

The following traits have been repeatedly observed and represent the characteristics of the new *Dianthus* cultivar 'WP15 PIE41'. 'WP15 PIE41' has not been tested under all possible conditions and phenotypic differences may be observed with variations in environmental, climatic and cultural conditions, however, without any variance in genotype.

1. 'WP15 PIE41' exhibits a compact mounding habit.
2. 'WP15 PIE41' bears single white flowers with a lime-colored eye.
3. The petals of 'WP15 PIE41' are flat.
4. 'WP15 PIE41' blooms from May through October.

5. The flowers of 'WP15 PIE41' exhibit a medium, sweet fragrance.
6. 'WP15 PIE41' exhibits glaucous blue green foliage.
7. At maturity, the height of the foliage mound of 'WP15 PIE41' is about 35 cm, and the width is about 20 cm.
8. 'WP15 PIE41' is perennial and is hardy at least to minus 15° Centigrade.
9. 'WP15 PIE41' is suitable for use as a flowering plant in pots and containers, and for use as a cut flower and in bouquets.

BRIEF DESCRIPTION OF THE PHOTOGRAPHS

The accompanying color photographs illustrate the overall appearance of the new *Dianthus* variety 'WP15 PIE41' showing colors as true as it is reasonably possible to obtain in colored reproductions of this type. Colors in the photographs may differ from the color values cited in the detailed botanical description, which accurately describe the actual colors of the new variety 'WP15 PIE41'.

Figure 1:
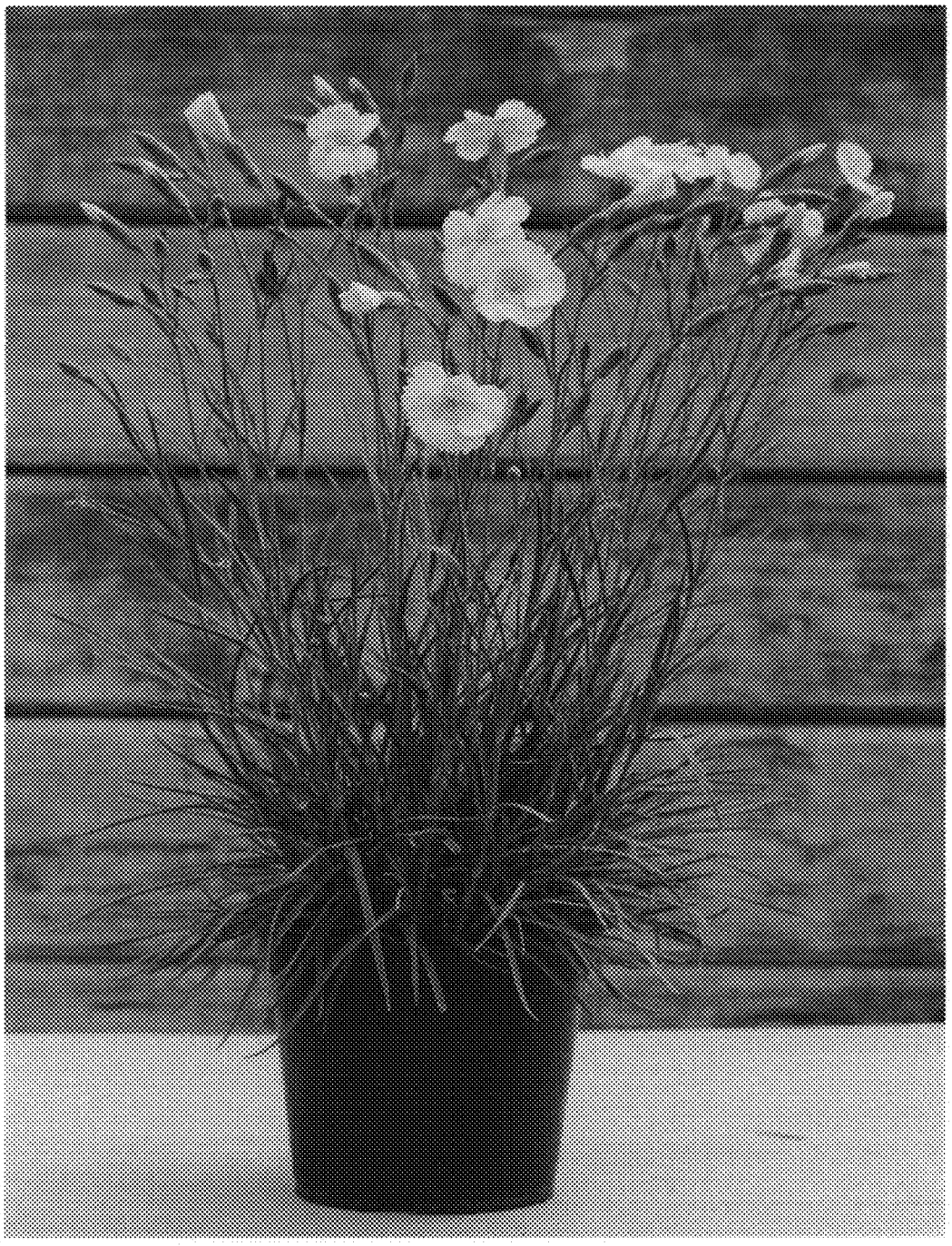
FIG. 1 depicts an entire flowering plant of 'WP15 PIE41'.
Figure 2:
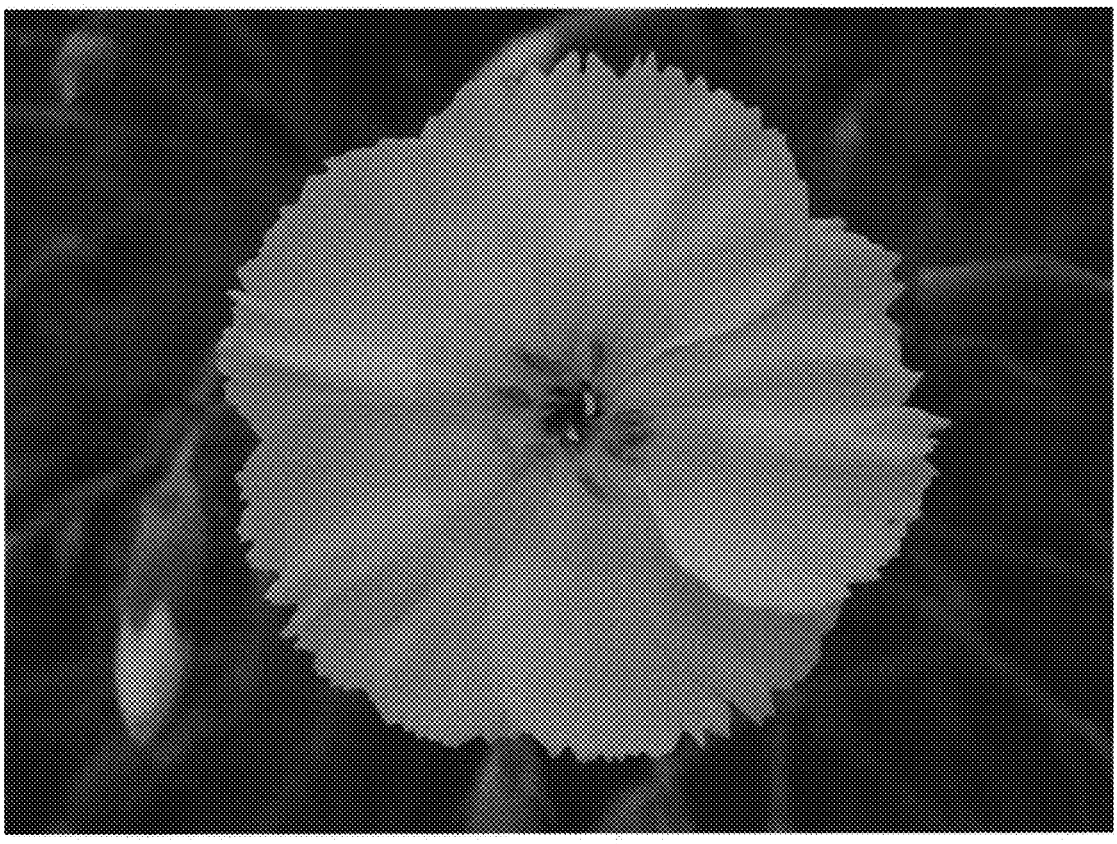
FIG. 2 depicts a close-up view of the flower of 'WP15 PIE41'.

Photographs were taken from a 9 months old plant which was growing in a glasshouse in a 3-liter container at the Inventor's nursery in Dawlish, Devon, United Kingdom. No chemicals were used to treat the plants.

All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'WP15 PIE41'. Data was collected from plants grown in 3-liter containers under an unheated glasshouse in Houndspool, Dawlish, United Kingdom. The color determinations are in accordance with the sixth edition (2015) of The Royal Horticultural Society Colour Chart of The Royal Horticultural Society, London, England, except where general color terms of ordinary dictionary significance are used. No chemicals were used to treat the plants. Growing conditions are typical to other *Dianthus*.

Botanical classification: *Dianthus*.

*Variety*.—'WP15 PIE41'.

*Species*.—x *allwoodii* hort.

*Common names*.—Hybrid *dianthus*, Garden Pink.

*Commercial classification*.—Hardy perennial.

*Use*.—Ornamental plant for pots and containers.

Parentage: 'WP15 PIE41' is a hybrid plant that resulted from the open pollination of the experimental *Dianthus* x *allwoodii* plants 'PIE.017' (unpatented).

Plant description:

*Bloom period*.—May to October.

*Plant habit*.—Compact mounding habit.

*Plant height*.—About 35 cm in overall height, including flower canopy.

*Plant width*.—About 20 cm in width.

*Plant hardiness*.—Hardy to minus 15° Centigrade.

*Type*.—Perennial.

*Root system*.—Fibrous.

*Propagation*.—Propagation is accomplished using shoot cuttings.

*Cultural requirements*.—Plant in full sun, well-drained and moderately fertile soil and keep well fertilized and watered.

*Time required to produce a rooted cutting*.—5 weeks are needed to produce a rooted cutting.

*Temperature recommended for cuttings to produce roots*.—The air temperature needed is a minimum of 15° Centigrade air temperature and base heat of 21° Centigrade.

*Crop time*.—6 to 9 months is needed to produce a finished 3-liter container size from a well-rooted cutting.

Stem:

*Shape*.—Cylindrical, solid.

*Dimensions*.—12 cm in length, 6 mm diameter.

*Surface*.—Glabrous and glaucous.

*Color*.—145B and 145C.

*Branching*.—Numerous shoots from the axils of the lower leaves.

*Internode length*.—4 mm to 6 mm between nodes (before extension of peduncle).

*Node dimensions*.—6 mm in diameter and 3 mm in length.

Leaf:

*Type*.—Evergreen.

*Dimensions*.—10 cm in length, 2 mm in width.

*Color* (*adaxial and abaxial surfaces*).—N189C.

*Shape*.—Linear.

*Division*.—Simple.

*Apex*.—Acute.

*Base*.—Decurrent.

*Venation*.—Absent on the adaxial surface and only one central vein visible on the abaxial surface.

*Margins*.—Entire.

*Attachment*.—Sheathing.

*Arrangement*.—Opposite and spiraling up stem.

*Curvature*.—Weakly recurved.

*Surfaces* (*adaxial and abaxial*).—Strongly glaucous.

*Fragrance*.—Absent.

Flowers:

*Inflorescence*.—Simple cyme.

*Type*.—Single, polypetalous.

*Number*.—3 to 6 per stem.

*Dimensions* (*including calyx*).—35 mm in length and 52 mm in diameter.

*Shape*.—Circular.

*Position*.—Flowers are borne far above the foliage.

*Internodes*.—On average (5 flowering stems), each stem presents 4 internodes between the lowest flower-bearing node and epicalyx.

*Lastingness*.—10 days at 20° Celsius on the plant; 8 to 10 days off the plant.

*Fragrance*.—Medium, sweet.

*Flowering period*.—May to October.

Peduncle:

*Shape*.—Cylindrical, solid.

*Dimensions*.—20 cm to 25 cm in length, 2 mm in diameter.

*Surface*.—Glabrous, waxy.

*Strength*.—Strong, rigid.

*Color*.—N189B-N189C.

Bud:

*Shape*.—Cylindrical.

*Color*.—N189B on apical half and 144B on basal half (below the bracts).

*Anthocyanin*.—Absent.

*Dimensions*.—About 28 mm in length and 8 mm in width.

Petals:

*Corolla.*—Upper and lower part of corolla is flat.

*Petal arrangement.*—Persistent, apopetalous and overlapping.

*Margin.*—Crenate-dentate.

*Indentations.*—Up to 2 mm deep, often narrower.

*Texture.*—Soft.

*Type.*—Single.

*Number of petals.*—5.

*Dimensions.*—About 55 mm in length, 32 mm in width.

*Petal shape.*—Fan shape.

*Petal undulation* (*side view*).—Moderate undulation.

*Petal surface.*—Glabrous.

*Petal apex.*—Fan shaped, crenate-dentate, moderate number of indents.

*Petal base.*—Strap shaped, tapering towards base.

*Color pattern.*—Blade is white, with a yellow-lime green band.

*Petal color* (*adaxial surface*).—Ground color of blade: NN155D. Color of band (considered to overlay the blade): Progressing from 150C when flower freshly open through 149D, 145C to 150D when flower is fully open and mature. Color of middle of strap: 145C. Color of base of strap: 145D.

*Petal color* (*abaxial surface*).—Ground color of blade: NN155D. Overlaying band: Absent on abaxial surface. Color of middle of strap: 145C. Color of base of strap: 145D.

Calyx:

*Dimensions.*—32 mm in length and 8 mm in width.

*Shape.*—Cylindrical.

*Sepals.*—5, fused to 8 mm below the apex.

*Sepal dimensions.*—33 mm in length and 6 mm in width.

*Apex.*—Acute.

*Base.*—Truncate.

*Color of sepals, outer surface.*—137C fading to 138B to 138C at base.

*Color of sepals, inner surface.*—139D.

*Anthocyanin.*—Absent.

*Splitting.*—Not observed.

Epicalyx:

*Arrangement.*—Two pairs of bracts, of which one pair (inner epicalyx or bracteoles) is closest to the calyx, and one pair forms an outer epicalyx.

*Bracts shape.*—Acuminate.

*Bracts position.*—Both pairs adpressed to each other and to calyx, and free.

*Bracts dimensions* (*outer epicalyx*).—10 mm in length and 6 mm in width.

*Bracts dimensions* (*inner epicalyx*).—11 mm in length and 12 mm in width.

*Bracts color.*—N138C, N138D and 138D are all present.

*Bracts anthocyanin.*—Absent.

Reproductive organs:

*Stamen number.*—10.

*Stamen dimensions.*—31 mm length and 0.5 mm diameter.

*Color of filaments.*—NN155D.

*Anther number.*—10.

*Anther dimensions.*—4 mm length and 1 mm in diameter.

*Color of anthers.*—NN155D.

*Anther attachment.*—Dorsifixed.

*Pollen.*—Present, dust color closest to N155A.

*Style number.*—2.

*Style shoulder.*—Absent.

*Color of style.*—NN155D.

*Style dimensions.*—About 30 mm in length and 1 mm in width.

*Stigma number.*—One on each style.

*Stigma color.*—NN155D.

*Stigma dimensions.*—Along the top of the style, fimbriated zone when mature, 8 mm above petals at maturity.

*Ovary position.*—Superior.

*Ovary dimensions.*—11 mm in length and 6 mm in diameter.

*Ovary shape.*—Oblong.

*Ovary surface and texture.*—Smooth and slightly ribbed.

*Ovary color.*—145A to 145B at the uppermost surface, becoming paler to 149D at the lowest surface.

Seed:

*Color.*—202A.

*Length.*—3 mm.

*Diameter.*—2 mm.

*Shape.*—Oval and flattened.

*Surface.*—Crinkled.

*Number.*—Up to 20 per pod but can vary.

Diseases and pests: Susceptible to known *Dianthus* pests and disease but no other susceptibilities to pests or disease are known.

COMPARISON WITH PARENTAL LINE AND KNOWN VARIETY

'WP15 PIE41' is distinguishable from the female parent as follows. 'WP15 PIE41' has much shorter flower stems than its female parent and a much more compact plant habit. In addition, the color of the petals of the female parent 'PIE.017' is a white with a cream-pink band.

The variety of *Dianthus* considered to most closely resemble 'WP15 PIE41' is the inventor's variety *Dianthus* 'WP15 PIE45'(co-pending U.S. Plant patent application Ser. No. 15/731,061). In comparison with 'WP15 PIE45', 'WP15 PIE41' has slightly shorter stems and different flower color. Whereas the flowers of 'WP15 PIE41' are white with a lime-colored eye, the flowers of 'WP15 PIE45' are light peach in color with a darker peach band, the two colors being separated by a prominent red-orange line. In addition, the petal margins of 'WP15 PIE45' are more prominently indented.

I claim:

1. A new and distinct cultivar of *Dianthus* plant named 'WP15 PIE41' as described and illustrated herein.

* * * * *